US00PP10621P

United States Patent [19]

Delbard

[11] Patent Number: Plant 10,621

[45] Date of Patent: Sep. 29, 1998

[54] HYBRID TEA ROSE PLANT NAMED 'DELSTRIBUC'

[75] Inventor: Guy Delbard, Hyeres, France

[73] Assignee: Societe Anonyme des Pepinieres et Roseraies Georges Delbard, Commentry, France

[21] Appl. No.: 800,752

[22] Filed: Feb. 14, 1997

[30] Foreign Application Priority Data

Aug. 6, 1996 [FR] France ..... 15018

[51] Int. Cl.[6] ..... A01H 5/00

[52] U.S. Cl. ..... Plt./13

[58] Field of Search ..... Plt./11, 12, 13

[56] References Cited

PUBLICATIONS

UPOU–ROM, 1997 Apr., Plant Variety Database, GTI Jouve Retrieval Software, Citation for 'Delstribuc'.

*Primary Examiner*—Howard J. Locker

*Attorney, Agent, or Firm*—Burns, Doane, Swecker & Mathis, L.L.P.

[57] ABSTRACT

A new and distinct variety of Hybrid Tea rose plant is provided that abundantly forms attractive double flowers that are bright red velvet striped with yellow or white coloration. Such flowers are long lasting and possess petals that detach cleanly. The plant exhibits an upright to bushy growth habit, forms long straight stems, forms semi-vigorous to vigorous vegetation, and is particularly well suited for greenhouse forcing for cut flower production. Additionally, the plant is resistant to diseases when grown under greenhouse conditions.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) was the product of the pollination of the 'Aromaepi' variety (non-patented in the United States) and the 'Deladel' variety (U.S. Plant Pat. No. 4,391). The male parent (i.e., the pollen parent) was the 'Deladel' variety. The parentage of the new variety can be summarized as follows:

('Aromaepi'×'Deladel')×'Deladel'.

The seeds resulting from the above pollination were sown and 124 small plantlets were obtained which were physically and biologically different from each other. Selective study resulted in the identification of a single plant of the new variety.

It was found through careful study that the new variety of the present invention exhibits the following combination of characteristics:

(a) from a physical point of view forms green mature wood, assumes an upright to bushy growth habit, and forms attractive long-lasting bright red velvet double flowers that are striped with yellow or white having consistent petals, and (b) from the biological point of view forms semi-vigorous to vigorous vegetation, produces flowers in abundance, exhiits the ability readily to be forced, and is resistant to diseases when grown under greenhouse conditions.

The new variety well meets the needs of the horticultural industry and is particularly well suited for growing in the greenhouse for the production of attractive long-lasting cut flowers that are bright red velvet striped with yellow or white depending upon the season and the conditions of growth.

The new variety can be readily distinguished from other varieties in view of the combination of characteristics described herein. It exhibits long and straight stems, rigid and straight peduncles, a good ability to be forced under greenhouse conditions, and a long vase life for its distinctive bright red velvet blossoms.

For instance, the new variety of the present invention can be distinguished from 'Deladel'. The blossom configuration and number of petals are similar to those of 'Deladel'; however, the 'Deladel' variety exhibits a solid red velvet blossom coloration which is considerably different than the distinctive striped bright red velvet blossoms of the new variety. Also, the seedling of the cross between 'Aromaepi'× 'Deladel' is a Floribunda having blossoms that are light orange striped with white and some yellow.

The new variety has been found to undergo asexual propagation and can be readily reproduced by conventional routes, such as budding (i.e., eye grafting) and tissue culture. This asexual reproduction by budding and tissue culture as performed at Hyéres, France, has demonstrated that the characteristics of the new variety are strictly transmissible from one generation to another and are firmly fixed.

The new variety has been named the 'Delstribuc' variety.

BRIEF DESCRIPTION OF THE PHOTOGRAPH

The accompanying photograph shows as nearly true as it is reasonably possible to make the same in a color illustration of this character typical specimens of the plant parts of the new variety. The rose plants of the new variety were grown under glass in the South of France.

FIG. 1—illustrates a specimen of a single leaflet—plan view—upper surface;

FIG. 2—illustrates a specimen of a leaf with three leaflets—plan view—upper surface;

FIG. 3—illustrates a specimen of a leaf with five leaflets—plan view—upper surface;

FIG. 4—illustrates specimens of two leaves with seven leaflets—plan view—upper surface (left) and under surface (right);

FIG. 5—illustrates a specimen of a young shoot;

FIG. 6—illustrates a specimen of a main branch;

FIG. 7—illustrates a specimen of a flowering stem;

FIG. 8—illustrates a specimen of a floral bud at the opening of the sepals;

FIG. 9—illustrates a specimen of a floral bud in a more advanced stage of opening than as illustrated in FIG. 8;

FIG. 10—illustrates a specimen of a floral bud at the opening of the petals;

FIG. 11—illustrates a specimen of a flower at an early stage in the course of opening;

FIG. 12—illustrates a specimen of a flower in a more advanced stage of opening than as illustrated in FIG. 11;

FIG. 13—illustrates a specimen of a flower in a more advanced stage of opening than as illustrated in FIG. 12;

FIG. 14—illustrates a specimen of a flower in a more advanced stage of opening than as illustrated in FIG. 13;

FIG. 15—illustrates a specimen of a flower in a more advanced stage of opening than as illustrated in FIG. 14;

FIG. 16—illustrates a specimen of an open flower—plan view—reverse;

FIG. 17—illustrates a specimen of an open flower—plan view—obverse;

FIG. 18—illustrates a specimen of a fully open flower—plan view—reverse;

FIG. 19—illustrates a specimen of a fully open flower—plan view—obverse;

FIG. 20—illustrates a specimen of a floral receptacle showing the arrangement of the stamens and pistils; and FIG. 21—illustrates a specimen of a floral receptacle showing the arrangement of the pistils (stamens removed).

DETAILED DESCRIPTION

The chart used in the identification of the colors is that of The Royal Horticultural Society (R.H.S. Colour Chart). The description is based on the observation of plants grown under glass in the South of France. The coloration in common terms sometimes also is provided.

Class: Hybrid Tea.

Plant:

*Height.*—Plants which were pruned to a height of 1 m. produce floral stems having a length of approximately 30 to 80 cm., and an average length of approximately 60 cm.

*Habit.*—Upright to bushy.

Branches:

*Color.*—Young shoots: when approximately 20 cm. long, on the upper part exhibit a reddish coloration, Greyed-Purple Group 184A, with some green coloration, and on the lower part green coloration, Yellow-Green Group 146C. Floral stems: Yellow-Green Group 146B. Mature wood: Yellow-Green Group 146A.

*Thorns.*—Configuration: Concave on the upper edge and deep concave on the under edge. Quantity, length and frequency: on a typical stem having a length of 10 cm., there commonly are approximately 6 to 8 thorns of 6 to 10 mm., approximately 22 to 30 thorns of 3 to 6 mm., and many thorns (e.g., approximately 60 to 80) of 1 to 2.5 mm. The floral stems in areas where thorns are absent commonly are smooth and also bear some smooth hairs. Color: on young shoots of approximately 30 cm. in length, the thorns are Greyed-Purple Group 183B in coloration, on floral stems the coloration of the thorns is Greyed-Purple Group 183C, and on mature wood the coloration of the thorns is Greyed-Orange Group 165A (havana brown).

*Leaves.*—Number: Typical for the class. Size: medium. Stipules: adnate, medium and commonly with small serrations on the edges.

*Leaflets.*—Number: rarely 1, and commonly 3, 5 and 7. Size: medium. Shape: obtuse to rounded at the base of the terminal leaflet; convex in the cross-section; and weak in margin undulation. Serration: present, single, irregular, and not strongly marked. General appearance: thin with a medium glossiness on the upper surface of the leaflets. Petiole: the inner surface is grooved with non-glandular edges. Petiole color on young shoot: bronze with reddish coloration on the inner surface and greenish-bronze on the outer surface. Petiole color on floral stem: Yellow-Green Group 146B on inner surface, and Yellow-Green Group 146C on outer surface. Petiole color on mature wood: Yellow-Green Group 146B on inner surface, and Yellow-Green Group 146C on outer surface. Petiole length of terminal leaflet: approximately 15 to 18 mm., approximately 16 mm. on average, with a standard deviation of 2 mm. Terminal leaflet length: approximately 60 to 87 mm., approximately 75 mm. on average, with a standard deviation of 10 mm. Terminal leaflet width: approximately 33 to 50 mm., approximately 42 mm. on average, with a standard deviation of 3 mm. Terminal leaflet shape at base: obtuse to rounded. Leaflet color of young shoot: the first upper leaf is reddish with brown coloration and becomes green with brown coloration blending with reddish coloration at the margins. At the base the upper surfaces of the leaves approach Green Group 137C. The under surfaces are Greyed-Purple Group 184A for the three upper leaves and become green with reddish coloration at the base. Leaflet color on floral stem: Yellow-Green Group 147A on the upper surface and Yellow-Green Group 147C on the under surface. Leaflet color of mature wood: Yellow-Green Group 147A on the upper surface, and Yellow-Green Group 147C on the under surface.

Inflorescence:

*Number of flowers.*—Generally one per stem when grown under forced greenhouse conditions; however, three to four buds on the upper part of the stem commonly appear with the central bud under forced culture conditions.

*Peduncle.*—Erect, stiff, green in coloration with some hairs, and commonly approximately 6 to 12 cm. in length (approximately 10 cm. in length on average).

*Sepals.*—Configuration: as indicated in FIG. 8, before the calyx breaks the sepals are not separated at the base, and as the bud opens initially 3 sepals and subsequently 5 sepals can be distinguished. Two sepals commonly possess no extensions, one sepal commonly possesses very weak extensions, one sepal commonly possesses weak-to-medium extensions, and one sepal commonly possesses strong-to-very strong extensions. The sepal length commonly ranges from approximately 30 to 52 mm.; however, lengths as great as 72 mm. have been observed when a strong extension is present. Color: Yellow-Green Group 146D on the upper surface and Yellow-Green Group 146B on the under surface.

*Buds.*—Shape: ovate. Size before calyx breaks: the bud lengths are approximately 31 to 45 mm., with an average length of approximately 34 mm. Color as calyx breaks: dark pink, Red Group 53C to 53D and irregularly striped with yellow cream, Yellow Group 8D as the first petals of the second row open. Size after calyx breaks: the bud lengths are approximately 41 to 57 mm., with an average length of approximately 50 mm. Color after calyx breaks: inside: bright red velvet, Red Group 45A, and irregularly striped with Yellow Group 8B to white depending upon the season and the level of fertilization. outside: dark pink, Red Group 53D, and irregularly striped with white.

*Flower.*—Time: medium flowering. Shape: double. Form: round to irregularly rounded when viewed from above, flattened convex at the upper part when viewed from the side, and flattened convex at the lower part when viewed from the side. Diameter: medium to large, approximately 8.5 to 11.2 cm., and approximately 9.8 cm. on average, with a standard deviation of 1 cm. Petal number: commonly approximately 35 to 40, and an average of approximately 38. Petal size (second row from outside): the length is approximately 42 to 53 mm. with a means of approximately 45 mm., and a standard deviation of 0.2 mm.; and the width is approximately 42 to 62 mm. with a mean of approximately 46 mm., and a standard deviation of 0.5 mm. Petal shape: broad ovate with medium reflexing of the margin and medium undulation of the margin. Petal color: The following description of a nearly fully open flower was made while observing a rose grown in the greenhouse during November which had been undergoing opening for 3 days. In each instance the blossoms were striped. petal color (middle zone): on the inner surface bright red velvet, Red Group 45A, striped with Yellow Group 8B to 8D to white depending upon the level of fertilization and exposure to light, and on the outer surface dark pink, Red Group 53D, striped with cream, Yellow Group 8D, to nearly white depending upon the level of fertilization and exposure to light. petal color (marginal zone): on the inner surface bright red velvet, Red Group 45A, and white to cream at the striped area, and on the outer surface dark pink, Red Group 53D, and white at the striped area. Petal spot at base: small. Color of spot inner side: Yellow Group 8A to 8B. Color of spot outer side: Yellow Group 8C. Stamens: approximately 220 in number and are somewhat regularly arranged around the pistils. Filaments: medium in length and Yellow Group 13A in coloration. Anthers: medium in size, each opens at approximately the same time, and the immature coloration is deep yellow, Yellow-Orange Group 15A. Pollen: normal in quantity and Yellow Group 4D in coloration. Pistils: approximately 120 in number. Styles: medium in length and Yellow Group 10D in coloration. Stigmas: Yellow Group 10C, and generally extend slightly above the anthers. Hips: no hips have been observed to date. Seeds: none to date. Petal drop: petals detach clearly. Fragrance: very slight. Commonly a pine-like fragrance is transferred to the finger when a bud is touched. Lasting quality: long. When cut and placed in a vase, the flowers commonly last approximately 10 to 14 days.

Development:

*Vegetation.*—Semi-vigorous to vigorous.

*Blooming.*—Abundant and almost continuous.

*Aptitude to forcing.*—Good. Under greenhouse growing conditions at Hyéyres, France, approximately 100 to 110 blooms commonly are produced per square meter per year.

*Resistance to diseases.*—Good under greenhouse conditions, and sensitive to powdery mildew when grown outdoors.

I claim:

1. A new and distinct variety of Hybrid Tea rose plant characterized by the following combination of characteristics:

(a) from a physical point of view forms green mature wood, assumes an upright to bushy growth habit, and forms attractive long-lasting bright red velvet double flowers that are striped with yellow or white having consistent petals, and (b) from the biological point of view forms semi-vigorous to vigorous vegetation, produces flowers in abundance, exhibits the ability readily to be forced, and is very resistant to diseases when grown under greenhouse conditions, substantially as herein shown and described.

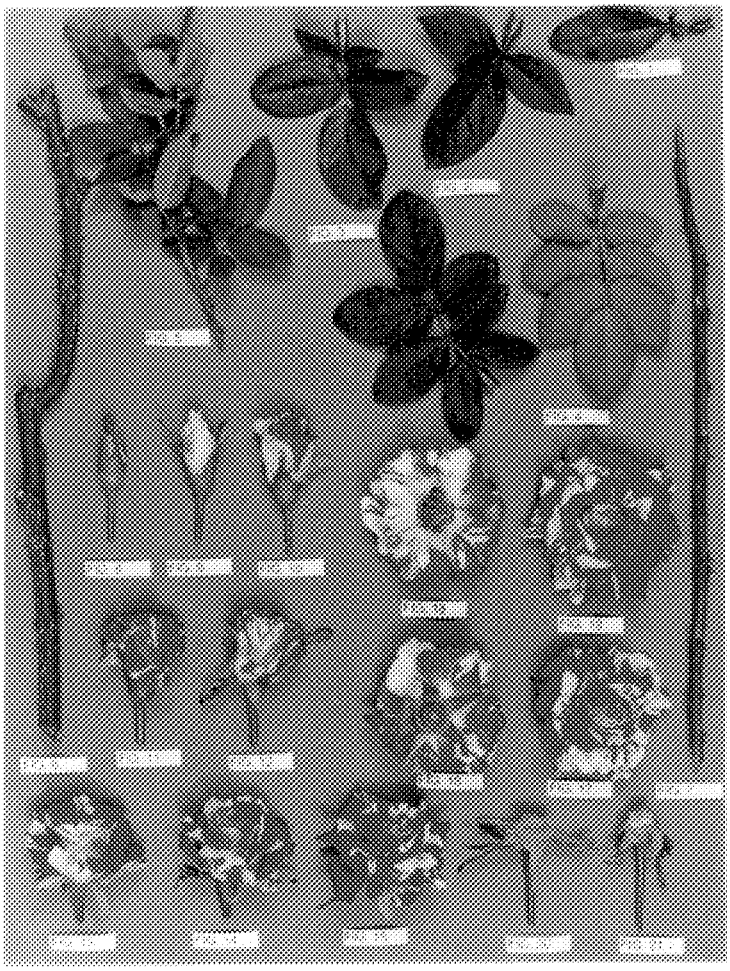

* * * * *